(12) United States Patent
Borgya et al.

(10) Patent No.: US 7,807,380 B2
(45) Date of Patent: *Oct. 5, 2010

(54) METHOD OF DETECTING A SUBFRACTION OF PROBNP

(75) Inventors: Anneliese Borgya, Seeshaupt (DE); Andreas Gallusser, Penzberg (DE); Michael Grol, Feldafing (DE); Klaus Hallermayer, Feldafing (DE); Volker Klemt, Weilheim (DE); Christoph Seidel, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/634,286

(22) Filed: Dec. 5, 2006

(65) Prior Publication Data

US 2007/0099241 A1    May 3, 2007

Related U.S. Application Data

(63) Continuation of application No. 11/271,651, filed on Nov. 10, 2005, now Pat. No. 7,264,939, which is a continuation of application No. PCT/EP2004/005092, filed on May 12, 2004.

(30) Foreign Application Priority Data

May 12, 2003    (EP) .................................. 03010591

(51) Int. Cl.
| | |
|---|---|
| G01N 33/53 | (2006.01) |
| G01N 33/577 | (2006.01) |
| C07K 16/26 | (2006.01) |
| C12N 5/20 | (2006.01) |
| C12P 21/08 | (2006.01) |
| G01N 33/543 | (2006.01) |

(52) U.S. Cl. ...................... 435/7.1; 435/7.92; 435/7.93; 435/7.94; 435/7.95; 435/70.21; 435/336; 435/452; 435/975; 436/518; 436/528; 436/531; 436/548; 436/811; 530/387.9; 530/388.24

(58) Field of Classification Search ................. 435/7.1, 435/7.92, 7.93, 7.94, 7.95, 70.21, 452, 336, 435/975; 436/518, 531, 547, 548, 811; 530/387.9, 530/388.24, 389.2

See application file for complete search history.

(56) References Cited

U.S. PATENT DOCUMENTS

| | | | |
|---|---|---|---|
| 5,786,163 | A | 7/1998 | Hall |
| 7,264,939 | B2 * | 9/2007 | Borgya et al. ................. 435/7.1 |
| 2003/0219734 | A1 | 11/2003 | Buechler |
| 2004/0096920 | A1 * | 5/2004 | Davey et al. ............... 435/7.92 |

FOREIGN PATENT DOCUMENTS

| | | |
|---|---|---|
| EP | 0186799 A1 | 7/1986 |
| EP | 0542255 A1 | 5/1993 |
| WO | WO 93/24531 | 12/1993 |
| WO | WO 00/35951 | 6/2000 |
| WO | WO 00/45176 | 8/2000 |

OTHER PUBLICATIONS

Buckley, M. et al. "Prolonged stability of brain natriuretic peptide: importance for non-invasive assessment of cardiac function in clinical practice," Clinical Science (1988) 95, 235-239.
Cleland, J. et al., "Stability of plasma concentrations of N and C terminal atrial natriuretic peptides at room temperature," Heart 75 (1996) 410-413.
Hughes, D. et al., "An immunoluminometric assay for N-terminal pro-brain natriuretic peptide: a development of a test for left ventricular dysfunction," Clinical Science (1999) 96, 373-380.
Hunt, P. et al., "The Amino-Terminal Portion of pro-Brain Natriuretic Peptide (Pro-BNP) Circulates in Human Plasma," Biochemical and Biophysical Research Communications, vol. 215, No. 3 (1995) 1175-1183.
Hunt, P., et al., "Immunoreactive amino-terminal pro-brain natriuretic peptide (NT-PROBNP): a new marker of cardiac impairment," Clinical Endocrinology (1997) 47, 287-296.
Hunt, P. et al., "The Role of Circulation in Processing pro-Brain Natriuretic Peptide (proBNP) to Amino-Terminal BNP and BNP-32," Peptides, vol. 18, No. 10 (1997) 1475-1481.
Köhler, G. et al., "Continuous cultures of fused cells secreting antibody of predefined specificity," Nature 256 (1975) 495-497.
Mair, J. et al., "The Impact of Cardiac Natriuretic Peptide Determination of the Diagnosis and Management of Heart Failure," Clin. Chem. Lab Med 2001, 39, (7): 571-588.
Mair, J. et al., "Role of Cardiac Natriuretic Peptide Testing in Heart Failure," Clinical Chemistry 48, No. 7, 2002, 977-978.
Masuta, C. et al., "Cardiac Markers," Clin. Chem. 44 (1998) 130.
Marrifield, R. et al., Federation of American Societies for Experimental Biology, 46th Annual Meeting, Atlantic City, NJ, Apr. 14-18, 1962, Abstracts of papers, 412.
Pemberton, C. et al., "Amino-terminal proBNP in ovine plasma: evidence for enhanced secretion in response to cardiac overload," Am. J. Physiol. 275 (4) Part 2 (1988) H1200-H1208.
Sudoh, T. et al., "A new natriuretic peptide in porcine brain," Nature 332(Mar. 3, 1988) 78-81.
Tsuji, T. et al., "Stabilization of Human Brain Natriueretic Peptide in Blood Samples," Clin. Chem. 40 (1994) 672-673.
Tijssen, P., "Practice and Theory of Enzyme Immunoassay," 11 (1990), pp. 43-78, especially pp. 43-47, Elsevier, Amsterdam.
Goetze, J. et al., "Quantification of Pro-B-Type Natriuretic Peptide and Its Products in Human Plasma by Use of an Analysis Independent of Precursor Processing," Clinical Chemistry 48:7 (2002) p. 1035-1042.

* cited by examiner

*Primary Examiner*—Shafiqul Haq
*Assistant Examiner*—James L Grun
(74) *Attorney, Agent, or Firm*—Marilyn L. Amick; Roche Diagnostics Operations, Inc.

(57) ABSTRACT

The present invention relates to antibodies specifically binding to native proBNP, a method for specific detection of native proBNP, a method of correlating the level of native proBNP to the diagnosis of heart failure, a kit for detection of native proBNP and to a hybridoma cell line producing an antibody to native proBNP.

4 Claims, 9 Drawing Sheets

Fig. 2a

Program for the determination of NT-proBNP in 20 patient samples with 8 different antibodies in BIACORE written and to be executed with BIACORE 3000 Control Software Version. 4.1

DEFINE APROG Sandwich
PARAM %apo %anr %aco %bnr %bco %c1po %c1nr %c1co %c2po %c2nr %c2co %c3po %c3nr %c3co %c4po %c4nr %c4co KEYWORD anr %anr
KEYWORD aco %aco
KEYWORD bnr %bnr
KEYWORD bco %bco
KEYWORD c1nr %c1nr
KEYWORD c1co %c1co
KEYWORD c2nr %c2nr
KEYWORD c2co %c2co
KEYWORD c3nr %c3nr
KEYWORD c3co %c3co
KEYWORD c4nr %c4nr
KEYWORD c4co %c4co CAPTION Sandwich: AG: %anr %aco mit %bnr %bco, AB: %c1nr, %c2nr, %c3nr, %c4nr

```
    FLOW      10 -f
    FLOWPATH  1,2,3,4

DIPNEEDLE r2e1
  * QUICKINJECT %apo 100      !calibrator/human serum
-0:10 RPOINT    -b BL_start FLOW      100
  * QUICKINJECT r2f6 50        !HBS FLOW      10 -f FLOWPATH  1
    DIPNEEDLE r2e2
  * QUICKINJECT %c1po 30       !AB1/5
-0:10 RPOINT    -b AG FLOWPATH  2
    DIPNEEDLE r2e3
  * QUICKINJECT %c2po 30       !AB2/6
-0:10 RPOINT    -b AB1

FLOWPATH  3
    DIPNEEDLE r2e4
  * QUICKINJECT %c3po 30       !AB3/7

-0:10 RPOINT    -b AB2

FLOWPATH  4
    DIPNEEDLE r2e5
  * QUICKINJECT %c4po 30       !AB4/8
-0:10 RPOINT    -b AB3
```

Fig. 2b

```
        FLOWPATH  1,2,3,4
        FLOW      100

* QUICKINJECT r2f7 50      !HBS
 -0:10 RPOINT    -b AB4

FLOW      20

* QUICKINJECT r2e10 5      !HBSwash
      * QUICKINJECT r2f3 10      !100 mM HCl
      * QUICKINJECT r2f4 10      !100 mM phosphoric acid
      * QUICKINJECT r2f5 10      !100 mM phosphoric acid
        EXTRACLEAN
  3:30 RPOINT    BL_end          !baseline after regen.cycle
END DEFINE APROG Regen
   CAPTION regeneration cycle
        FLOW      20
        FLOWPATH  1,2,3,4
      * QUICKINJECT r2e10 5      !HBSwash
 -0:10 RPOINT    -b BL_start
      * QUICKINJECT r2f3 10      !100 mM HCl
      * QUICKINJECT r2f4 10      !100 mM phosphoric acid
      * QUICKINJECT r2f5 10      !100 mM phosphoric acid
  3:30 RPOINT    BL_end          !baseline after regen.cycle
END DEFINE LOOP AG
  LPARAM %apo    %anr     %aco      %bnr     %bco
  TIMES 1
!       %apo    %anr     %aco      %bnr     %bco
        r2a1    NT-proBNP 40nM     HoSer/CMD 20%/1mg/mL
        r2a2    NT-proBNP 20nM     HoSer/CMD 20%/1mg/mL
        r2a3    NT-proBNP 10nM     HoSer/CMD 20%/1mg/mL
        r2a4    NT-proBNP 5nM      HoSer/CMD 20%/1mg/mL
        r2a5    NT-proBNP 2.5nM    HoSer/CMD 20%/1mg/mL
        r2a6    NT-proBNP 0nM      HoSer/CMD 20%/1mg/mL
        r2b1    HuSer1    1:5      HBS/CMD   1mg/mL
        r2b2    HuSer2    1:5      HBS/CMD   1mg/mL
        r2b3    HuSer3    1:5      HBS/CMD   1mg/mL
        r2b4    HuSer4    1:5      HBS/CMD   1mg/mL
        r2b5    HuSer5    1:5      HBS/CMD   1mg/mL
        r2b6    HuSer6    1:5      HBS/CMD   1mg/mL
        r2b7    HuSer7    1:5      HBS/CMD   1mg/mL
        r2b8    HuSer8    1:5      HBS/CMD   1mg/mL
        r2b9    HuSer9    1:5      HBS/CMD   1mg/mL
        r2b10   HuSer10   1:5      HBS/CMD   1mg/mL
        r2c1    HuSer11   1:5      HBS/CMD   1mg/mL
        r2c2    HuSer12   1:5      HBS/CMD   1mg/mL
        r2c3    HuSer13   1:5      HBS/CMD   1mg/mL
        r2c4    HuSer14   1:5      HBS/CMD   1mg/mL
        r2c5    HuSer15   1:5      HBS/CMD   1mg/mL
```

Fig. 2c

```
    r2c6   HuSer16   1:5    HBS/CMD   1mg/mL
    r2c7   HuSer17   1:5    HBS/CMD   1mg/mL
    r2c8   HuSer18   1:5    HBS/CMD   1mg/mL
    r2c9   HuSer19   1:5    HBS/CMD   1mg/mL
    r2c10  HuSer20   1:5    HBS/CMD   1mg/mL
END

DEFINE LOOP AB
  LPARAM %c1po %c1nr %c1co %c2po %c2nr %c2co %c3po %c3nr %c3co %c4po %c4nr %c4co
  TIMES 1
    r1a1  AB1  500nM  r1a2  AB2  500nM  r1a3  AB3  500nM  r1a4  AB4  500nM
    r1b1  AB5  500nM  r1b2  AB6  500nM  r1b3  AB7  500nM  r1b4  AB8  500nM
END

MAIN
  RACK    2 Thermo_a
  RACK    1 Thermo_c detection 1,2,3,4

LOOP AB ORDER
       APROG    Regen
       unclog
    LOOP AG ORDER
       APROG    Sandwich %apo %anr %aco %bnr %bco %c1po %c1nr %c1co %c2po %c2nr %c2co
                %c3po %c3nr %c3co %c4po %c4nr %c4co
    ENDLOOP
  ENDLOOP APROG    Regen
   APPEND   continue
END
```

METHOD OF DETECTING A SUBFRACTION OF PROBNP

RELATED APPLICATIONS

This application is a continuation application of U.S. Ser. No. 11/271,651 filed Nov. 10, 2005, now U.S. Pat. No. 7,264,939 which is a continuation of PCT/EP2004/005092 filed May 12, 2004, which claims priority to EP 03010591.0 filed May 12, 2003.

FIELD OF THE INVENTION

The present invention relates to antibodies specifically binding to a subpopulation of total proBNP termed native proBNP, a method for specific detection of native proBNP, a method of correlating the level of native proBNP to the diagnosis of heart failure, a kit for detection of native proBNP and to a hybridoma cell line producing an antibody to native proBNP.

BACKGROUND OF THE INVENTION

Heart failure is a widespread phenomenon, especially in the western world. According to the Roche medical dictionary (Urban & Schwarzenberg, 1993), heart failure is the acute or chronic inability of the heart to generate the blood flow required for metabolism during exercise or even at rest or to assure the venous reflux (backward and forward failure). Thus the pump function of the heart is weak. The causes of heart failure are very complex. Among others, inflammatory and degenerative modifications of the cardiac muscle, coronary perfusion disorder, coronary infarction and injuries are to be mentioned here. This leads to modifications of the peripheral bloodstream, disorders of the breathing system, renal function, and electrolyte metabolism (edema,) and to a reduced performance of the muscular system of the skeleton.

According to the New York Heart Association (NYHA), heart failure is divided into the following NYHA classes using physical tests after effort: I means completely free from pain after normal physical effort, II means low limitation of the physical toughness, III means strong limitation of the physical toughness, IV means that with each physical activity, the insufficiency symptoms increase which most of the time also exist at rest.

For an effective medicament treatment of heart failure by means of glycosides, vasodilators, ACE inhibitors, and/or β-blockers, it is first of all necessary to exactly and correctly identify and diagnose heart failure, to classify it, if possible, according to the degree of severity, and to additionally monitor the course of treatment.

In the art, some serum markers are discussed as marker candidates for an early diagnosis of heart failure as, for example, ANP (atrial natriuretic peptide) hormone and proANP, CNP (C-natriuretic peptide), adrenomedullin, neuropeptide Y, endotheline, and BNP (brain natriuretic peptide). ANP and proANP theoretically would represent suitable markers for the diagnosis of heart failure; in practice they are, however, not very stable or only have a short half life in blood, which represents a serious drawback to routine diagnostic measurements (Buckley, M. G., et al., Clin. Sci. 95 (1998) 235-239; Cleland, J. G., et al., Heart 75 (1996) 410413).

A frequently cited and meaningful marker is BNP (brain natriuretic peptide). Originally, BNP was identified in the brain of pigs. It is a cardiac hormone which structurally and functionally resembles ANP (Sudoh, T., et al., Nature 332 (1988) 78-81). Human BNP, consisting of 32 amino acids, is mainly secreted by the heart ventricles and circulates in the human blood plasma. The use of BNP as a diagnostic marker is, for example, known from EP 542,255. BNP has an intramolecular disulfide bridge and is not a very stable analyte. This presumably is due to its physiological function as a hormone that must be broken down quickly. Therefore, its use as a diagnostic marker requires careful and special attention in sample collection and processing (Masuta, C., et al., Clin. Chem. 44 (1998) 130; Tsuji, T., et al., Clin. Chem. 40 (1994) 672-673).

The precursor molecule of BNP, i.e., proBNP, consists of 108 amino acids. proBNP is cleaved into the aforementioned 32 C-terminal amino acids (77-108) called BNP and the N-terminal amino acids 1-76 called N-terminal proBNP (or NT-proBNP). BNP, N-terminal proBNP (1-76) as well as further breakdown products (Hunt, P. J., et al., Biochem. Biophys. Res. Com. 214 (1995) 1175-1183) circulate in blood. Whether the complete precursor molecule (proBNP 1-108) also occurs in the plasma is not completely resolved. It is, however, described (Hunt, P. J., et al, Peptides, Vol. 18, No. 10 (1997), 1475-1481) that a low release of proBNP (1-108) in plasma is detectable but that, due to the very quick partial breakdown at the N-terminal end, some amino acids are absent.

As known from the art, the N-terminal proBNP (1-76) is considered a marker of heart failure.

WO 93/24531 and U.S. Pat. No. 5,786,163 describe an immunological method of identifying N-terminal proBNP and the antibodies used for it. In WO 93/24531, polyclonal antibodies (PABs) against one single peptide derived from the N-terminal proBNP are produced. It is shown that the antibodies produced bind to the immunization peptide (amino acids 47-64) in a competitive test format.

In the competitive test performed in WO 93/24531, the peptide 47-64 in a labelled form competes as a tracer with proBNP in a sample or the unlabelled peptide standard 47-64 for binding to polyclonal antibodies from rabbit serum. Only a moderate competition is reached after 48 hours of incubation, resulting in a lower limit of detection of approximately 250 fmol/ml. The long incubation times of this competitive test are not acceptable for routine measurements of the samples in automated laboratories.

Hunt, P. J., et al., Clinical Endocrinology 47 (1997) 287-296, also describe a competitive test for the detection of N-terminal proBNP. In this assay, a complex extraction of the plasma sample is necessary before the measurement can be performed; this may lead to the destruction of the analyte and erroneous measurements. The antiserum used is produced analogously to WO 93/24531 by immunization with a synthetic peptide. Hunt et al. produce the antiserum by immunization with the N-terminal proBNP amino acids 1-13, and a peptide consisting of amino acids 1-21 is used as a standard. For this test, long incubation times are necessary, too. After an incubation of 24 hours, a lower detection limit of 1.3 fmol/ml is reached.

Ng, L., et al., WO 00/35951 describe a further method for determining N-terminal proBNP. This method is based on use of antibodies raised against a synthetic peptide corresponding to amino acids 65 to 76 of human proBNP.

Hughes, D., et al., Clin. Sci. 96 (1999) 373-380, report on two different assays for N-terminal proBNP. In a first assay, a polyclonal antibody generated with an immunogen comprising a synthetic peptide corresponding to amino acids 65-76 of proBNP is used, whereas in a second assay, the polyclonal antibody was generated in analogy but to amino acids 37-49. According to the data produced by Hughes, D., et al., an antibody generated and reactive with the peptide corresponding to amino acids 37-49 of proBNP does not react with intact endogenous proBNP. An assay based thereon does not discriminate patients with left ventricular dysfunction from normal controls. With the assay based on proBNP 65-76, the same patient groups could be clearly discriminated.

Goetze, J. P., et al., *Clin. Chem.* 48 (2002) 1035-1042, describe an assay for the most N-terminal amino acids (1-21) of N-terminal proBNP. Their assay is based on a polyclonal antibody raised against a synthetic peptide corresponding to the same amino acids (1-21) of proBNP.

The assay of Goetze, J. P., et al., supra, requires complete digestion of the sample and the various proBNP's comprised therein. It is said that this assay also was efficient in reduction of non-specific binding.

Karl, J., et al., WO 00/45176, for the first time show that sensitive and rapid detection of N-terminal proBNP is possible in a sandwich immunoassay. Preferred epitopes, as described in WO 00/45176, are between amino acids 10 and 50 of N-terminal proBNP. US 2003/0219734 refers to the fact that a plurality of different BNP-related polypeptides derived from proBNP (1-108), BNP (77-108), as well as from N-terminal proBNP (1-76) may be present in a sample. Mair, J., et al., *Clin. Chem. Lab. Med.* 39 (2001) 571-588, have summarized the impact of cardiac natriuretic peptide determination on the diagnosis and management of heart failure. They stress that currently available commercial assays are not standardized, i.e., they have not been calibrated against common standards. In some assays even an extraction of plasma is needed. Consequently, the results obtained with assays from different manufacturers may differ markedly. Therefore, reference intervals and decision limits derived from clinical studies are only valid for the particular assay used and must not be extrapolated to other assays for N-terminal proBNP.

Along the same lines, Goetze, J. P., et al., supra and Mair, J., *Clin. Chem.* 48 (2002) 977-978, note that the discrepancies between different assays of N-terminal proBNP, both with respect to the values obtained as well as with regard to their clinical implications, represent a crucial problem to the widespread use of this marker candidate.

Obviously a great need exists to provide for an improved, e.g., more reproducible, better standardized, better characterized, and more clinically relevant assay for N-terminal proBNP. It was a task of the present invention to develop a more specific assay for measurement of N-terminal proBNP and/or a clinically relevant fragment or subpopulation of N-terminal proBNP.

The invention as described below and claimed in the appending claims at least partially solves one or more of the problems known in the art.

SUMMARY OF THE INVENTION

It has surprisingly been found that it is possible to specifically detect a subpopulation of all proBNP species (total proBNP) present in the circulation. This subpopulation is termed "native N-terminal proBNP" or simply "native proBNP". Strikingly, it appears that the subpopulation of native proBNP is clinically more relevant as compared to the total proBNP.

In a first embodiment, the present invention relates to an isolated antibody specifically binding to native proBNP.

The invention also relates to a method for specific detection of native proBNP comprising the steps of contacting a sample suspected or known to contain proBNP with an antibody specifically binding to native proBNP under conditions allowing for the formation of an antibody to native proBNP-native proBNP complex and detecting the complex formed.

Further, the invention discloses a method for diagnosing heart failure comprising detection of native proBNP and correlating the level of native proBNP to heart failure, whereby this correlated value of native proBNP is indicative for the absence, the presence, or the status of heart failure.

The invention also relates to a kit for measurement of native proBNP comprising an antibody specifically binding to native proBNP and auxiliary reagents for detection of native proBNP. Also claimed are monoclonal antibodies specific for native proBNP as produced by hybridoma cell lines MAB 1.21.3 and MAB 16.1.39, respectively, which have been deposited with the Deutsche Sammlung von Mikroorganismen und Zellkulturen GmbH (DSMZ).

DESCRIPTION OF THE DRAWINGS

FIG. 2: Instrument settings used in the BIACORE analyses. The specificity for native proBNP of the various antibodies to proBNP has been assessed using the mode of operation of the BIACORE 3000 analyzer (Biacore AB, Sweden) as given in this figure.

DESCRIPTION OF THE INVENTION

Figure 1:
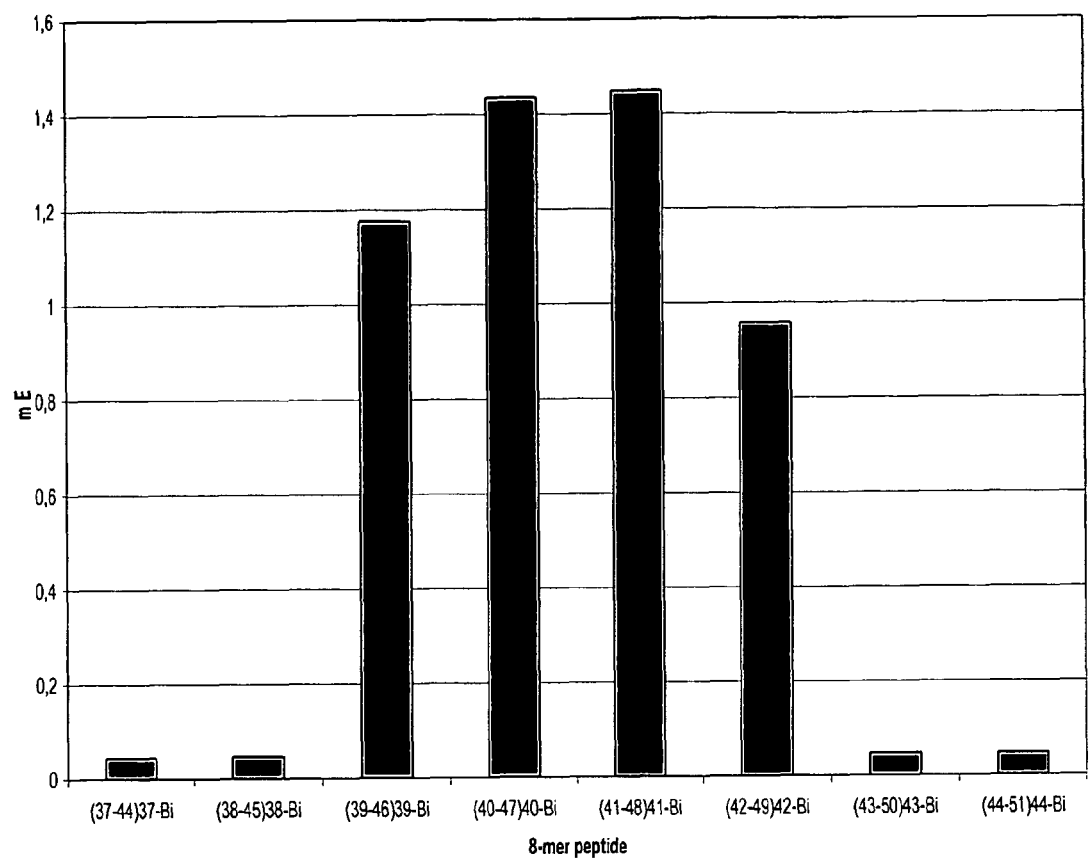
FIG. 1: Epitope identification for MAB 1.21.3. The reactivity profile of MAB 1.21.3 has been analyzed by use of 69 different biotinylated 8-mer peptides derived from the sequence of proBNP (1-76), each shifted by one amino acid thus covering the complete sequence of proBNP (1-76). Extinction is given in mE-units. Strong reactivity has been found to peptides numbers 39 to 42.
Figure 3:
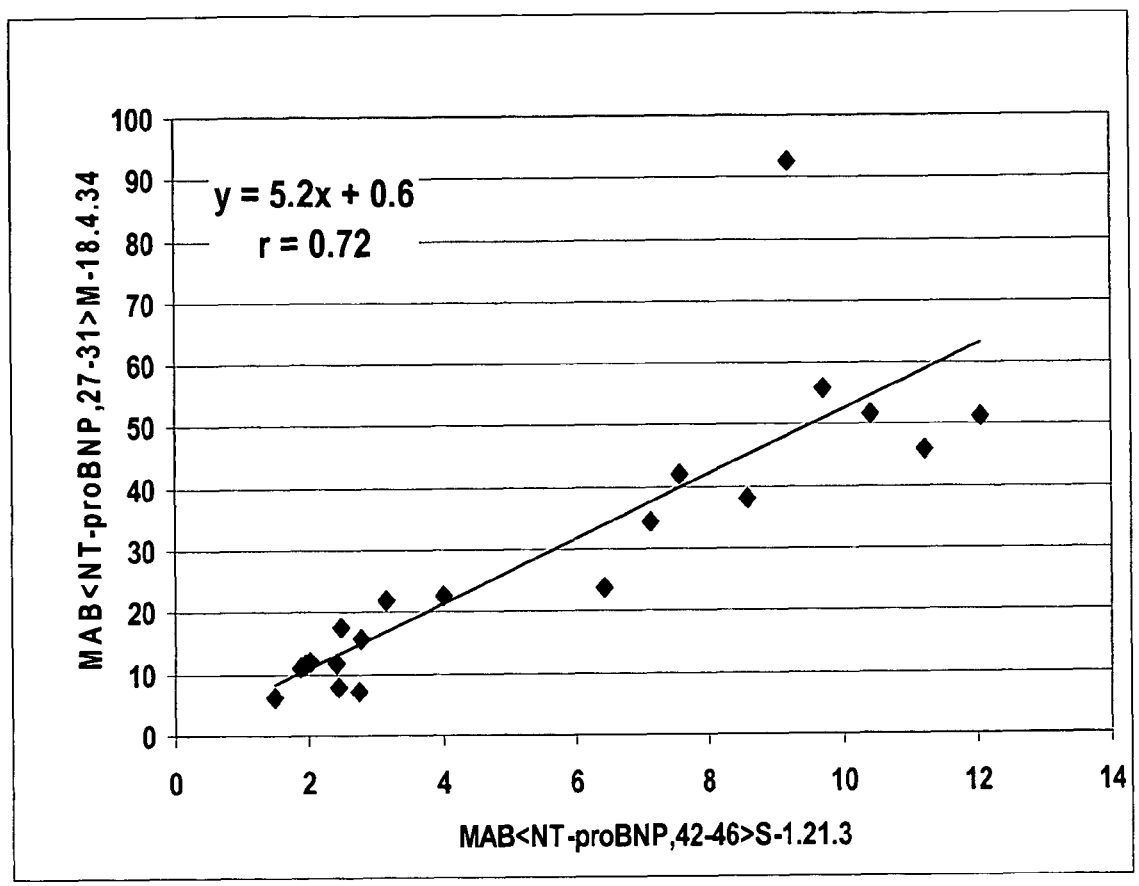
FIGS. 3 to 7: Correlation of MAB 1.21.3 to various mono- and polyclonal anti-proBNP antibodies. Twenty human sera with a concentration of proBNP of about 10 mg/ml and above (as determined by using MAB 1.21.3 and synthetic proBNP as a calibrator) have been analyzed in a sandwich assay using the BIACORE 3000 analyzer. Values measured with MAB 1.21.3 are given on the x-axis. The corresponding values determined with the antibody used in the method comparison are given in the y-axis. Correlations of MAB 1.21.3 to MAB 18.4.34, MAB 18.29.23, PAB 30-38, PAB 44-51 and PAB 41-46 are given in FIGS. 3, 4, 5, 6, and 7, respectively.
Figure 4:
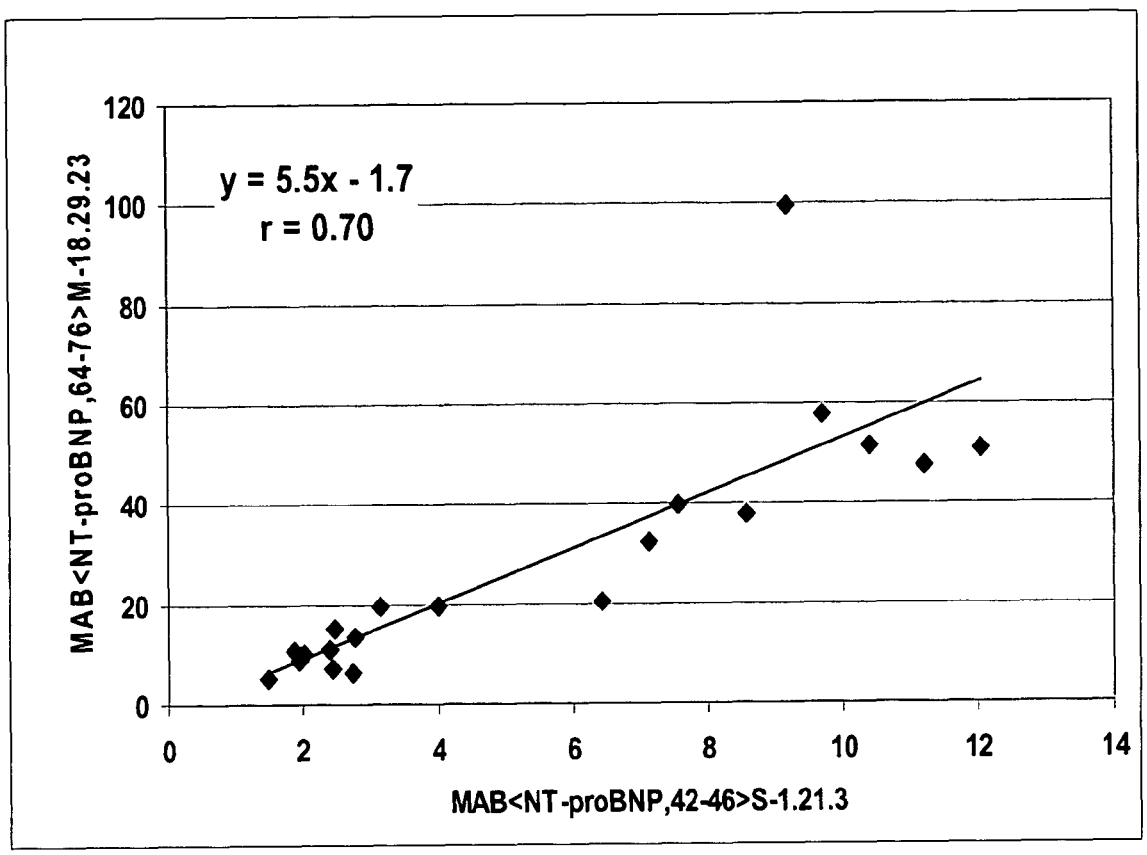
Figure 5:
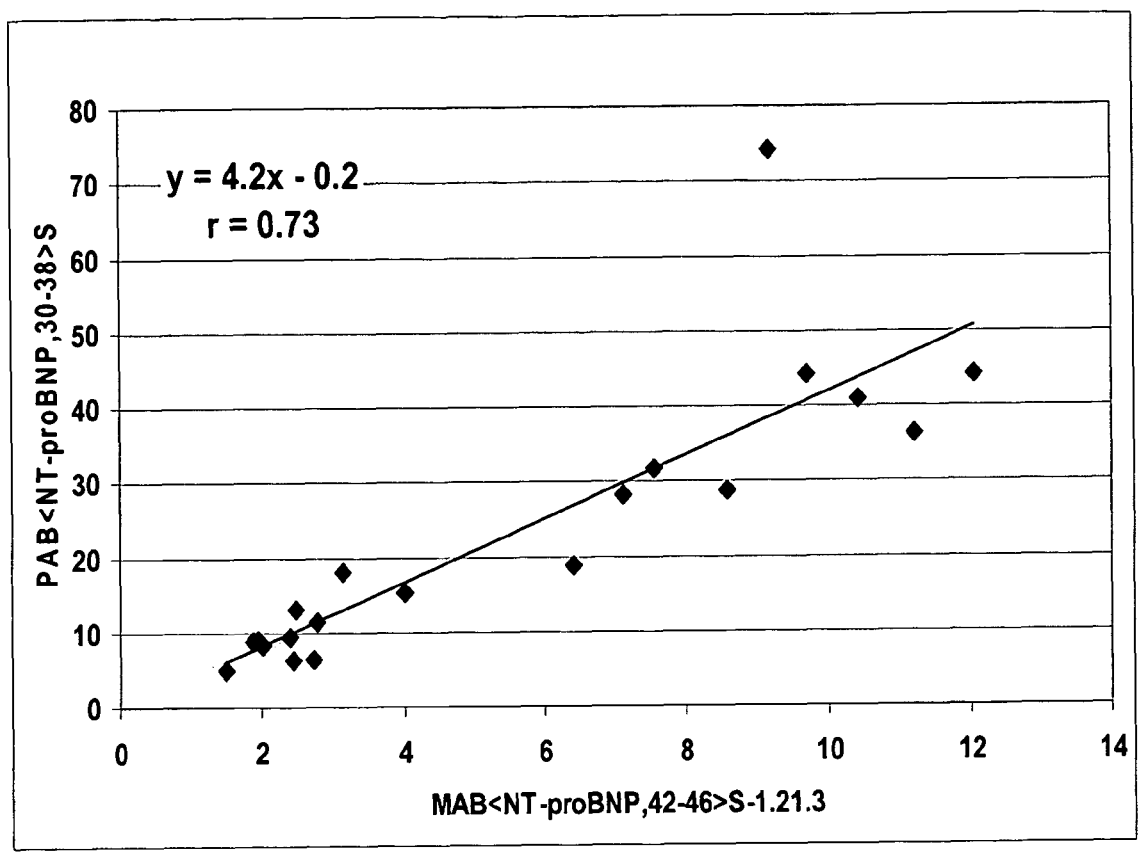
Figure 6:
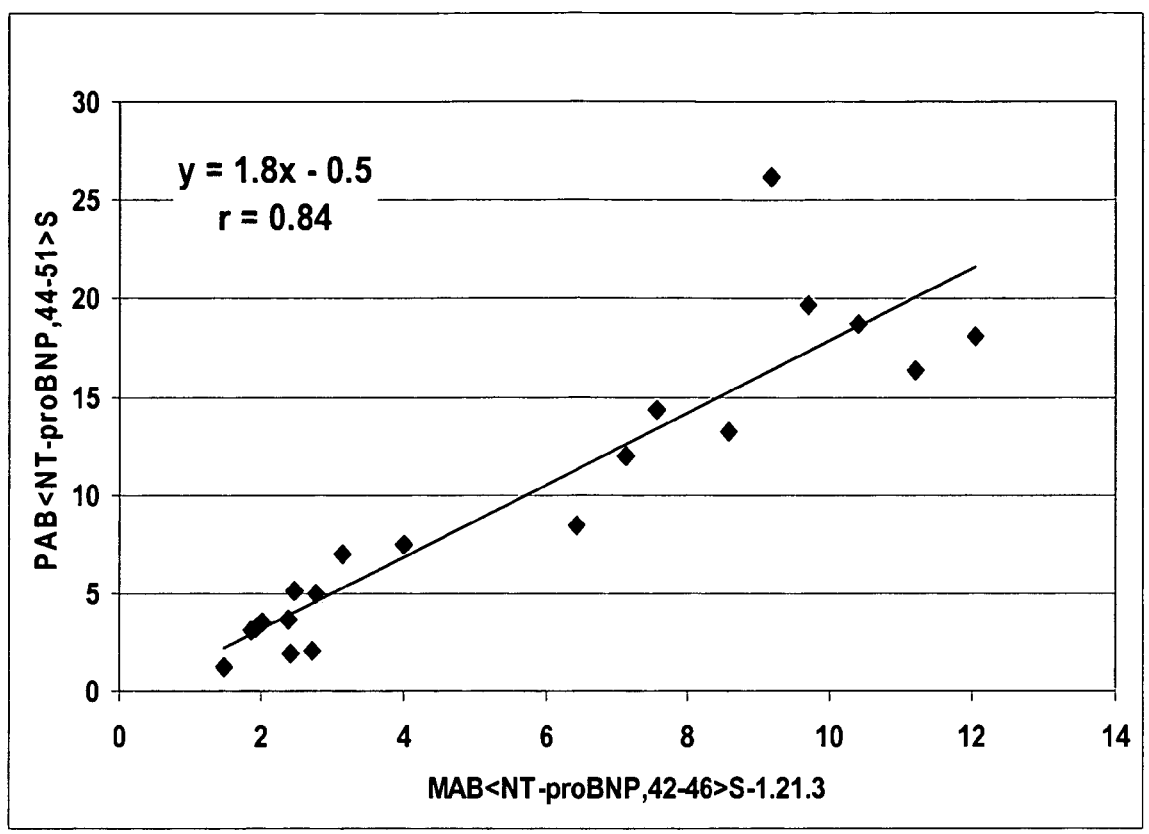
Figure 7:
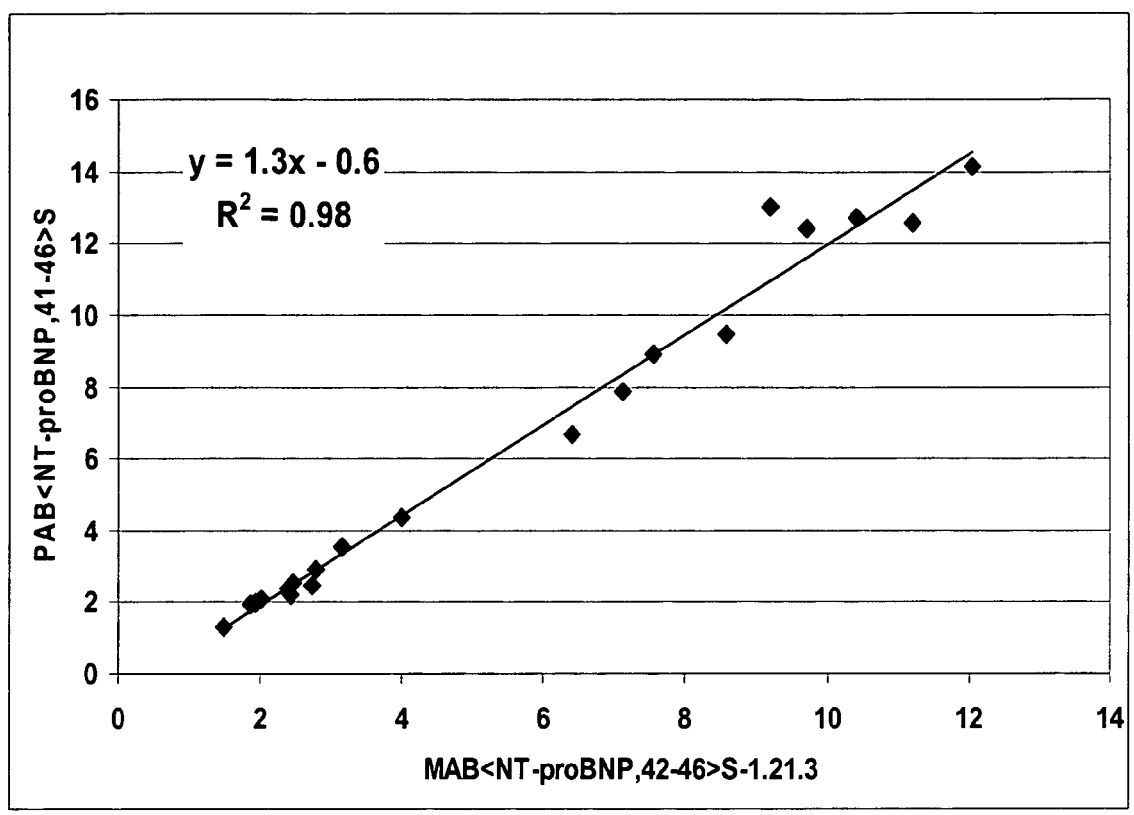

During the course of our experiments leading to the present invention, it has been found and established that at least two populations of proBNP exist in human blood. One population of proBNP appears to represent the majority of all proBNP molecules, which can be detected by immunological methods. This population is termed "total" proBNP. Our studies have shown that the proBNP molecules which may be summarized as total proBNP apparently have a central core structure in common which ranges from about amino acid position 10 to about amino acid position 66 of proBNP. Preferably the total proBNP detected by a method according to the present invention comprises amino acids 10 through 66. As the skilled artisan will appreciate, such total proBNP can be easily detected by immunological procedures either in a competitive or in a sandwich assay format. Preferably a sandwich assay is used to detect total proBNP. Such sandwich assay may be designed to comprise antibodies binding C- and N-terminal to the native proBNP epitope, respectively. However, it is also possible to, e.g., detect total proBNP using antibodies capable of sandwich formation and both reactive with epitopes N-terminal to the native proBNP epitope. Obviously, in such competitive or in such sandwich determination of total proBNP, an antibody to native proBNP must not be used.

The term "native proBNP" denotes any proBNP molecule on which the epitope as recognized by MAB 1.21.3 is present.

According to the findings demonstrated further below, this epitope is only present on a subpopulation of all proBNP-molecules, i.e., a subpopulation of "total" proBNP. We found and could establish that this subpopulation of total proBNP termed "native proBNP" is detectable by specific binding partners, preferably by polyclonal and/or monoclonal antibodies.

The subpopulation termed native proBNP must not necessarily be a uniform polypeptide fragment. The length of the native proBNP polypeptide(s) may vary. Most of the molecules recognized in a sandwich immunoassay for native proBNP are expected to represent N-terminal proBNP (1-76) or fragments thereof. Preferably an assay for native proBNP is set up in a manner appropriate for measurement of NT-proBNP fragments comprising amino acids 10 through 66. The characteristic property of native proBNP is the presence of a native proBNP epitope as recognized by MAB 1.21.3.

In one embodiment, the present invention relates to an antibody specifically binding to native proBNP, wherein said antibody specifically binding to native proBNP is an antibody which, in terms of the values for proBNP as determined in patient samples, correlates with an r value of at least r=0.95 or above to MAB 1.21.3.

Based on the findings, disclosure, and deposits of the present invention, the skilled artisan will have no problem in assessing whether an antibody is specifically binding to native proBNP or to total proBNP. MAB 1.21.3 is considered a prototype example of an antibody specifically binding to native proBNP, whereas MAB 18.4.34 is considered a prototype example of an antibody to total proBNP. Any binding agent to proBNP whatsoever can now be assessed for its binding specificity to native or total proBNP, respectively.

An antibody "specifically binding" to native proBNP is an antibody which, in terms of the values for proBNP as determined in patient samples, correlates with an r value of at least r=0.95 or above to MAB 1.21.3. Binding specificity to native proBNP is assessed in relation to the binding properties of MAB 1.21.3 using relevant clinical samples. At least 20 and at most 25 serum samples obtained from patients with an NT-proBNP level of 10 ng/ml to 150 ng/ml of native proBNP are used. Binding to proBNP is determined with the BIACORE 3000 system. The values measured are correlated to native proBNP values as measured using MAB 1.21.3, and the statistical assessment is performed by linear regression analysis. A linear regression of the type y=ax+b preferably is fitted using Microsoft Excel, and the coefficient of correlation r and the slope is calculated. Even more preferred, such antibody will detect essentially the same native proBNP subpopulation of total proBNP as bound by MAB 1.21.3, wherein a binding to the essentially the same subpopulation results in a correlation of r=0.98 or higher according to the above procedures.

MAB 18.4.34 may be considered a prototype antibody for measurement of total proBNP. For any antibody specifically binding to native proBNP, using the same samples and procedures as described above, the correlation to MAB 18.4.34, i.e., to total proBNP, typically will be lower as compared to the correlation to MAB 1.21.3. Preferably the correlation to MAB 18.4.34 for an antibody specifically binding to the native proBNP subfraction of proBNP will be r=0.94 or below. Even more preferred, it will be r=0.9 or below or as low as r=0.8 or below.

When comparing absolute amounts measured in such method comparisons, the assays detecting total proBNP consistently yield about 2- to 20-fold, in most cases about 2- to 5-fold, higher values of proBNP as compared to MAB 1.21.3. In addition to the above specified correlation, a preferred antibody specifically binding to native proBNP will in the above method comparison also show a slope of less than 1.5. Most preferred, the slope will be between 0.4 and 1.5.

The specific binding preferably occurs with a binding affinity of at least $10^7$ L/mol. The specific binding agent more preferred has an affinity of $10^8$ L/mol or even more preferred of $10^9$ L/mol for native proBNP.

As explained above, a very important and preferred characteristic of MAB 1.21.3 is the fact that only a variable fraction of between about 5% and about 50% of total proBNP as comprised in a typical clinical sample is bound by this antibody.

A prototype example of an antibody which specifically binds to native proBNP is the monoclonal antibody as produced by clone MAB 1.21.3 which has been deposited with the DSMZ. MAB 1.21.3 is a sheep monoclonal antibody and has been produced as described in the Specific Embodiments section. The epitope on proBNP recognized by these and by other antibodies has been identified, characterized, and mapped by use of short synthetic peptides corresponding to well-defined sequences of proBNP. This method is known and referred to as PepScan analysis.

In brief, 69 synthetic peptides comprising 8 consecutive amino acids of proBNP have been synthesized comprising an N-terminal cysteine, a spacer molecule, and biotin. Each of these peptides was shifted by one amino acid from the N- to the C-terminus. Peptide 1 thus comprises amino acids (aa's) 1 to 8, peptide 2, aa's from aa's 2 to 9, etc., and peptide 69, aa's 69 to 76. MAB 1.21.3 has been found to significantly react with peptides number 39 (amino acids 38-46) to 42 (aa's 42-49) which have the amino acid positions 42 to 46 of proBNP in common. It therefore can be concluded that MAB 1.21.3 reacts with an epitope essentially consisting of amino acids 42 to 46 of proBNP.

As the skilled artisan appreciates, the presence or absence of an epitope may depend on tertiary structure, secondary modifications, complex formation, accessibility, and so on. Obviously, MAB 1.21.3 and other antibodies to native proBNP have very specific requirements in this regard and do not react with the majority of proBNP-molecules present in a typical sample. Since the short synthetic PepScan peptides are unlikely to have a tertiary structure or secondary modifications the epitope recognized by MAB 1.21.3 should be unmodified, and the terminology "native" has therefore been considered appropriate.

An assay based on an antibody to native proBNP and an assay measuring total proBNP exhibit striking differences in reaction intensity once synthetic proBNP (1-76) and proBNP as comprised in a clinical sample, like human serum, respectively, are measured and compared. Using synthetic proBNP (1-76), detection procedures can easily be set up and standardized. Employing such assays, synthetic proBNP (1-76) either in a synthetic matrix or supplemented to a native sample, like human serum, is measured to the same levels in both these assays. Surprisingly, however, striking differences are found once proBNPas comprised in a native sample like human serum, is measured both these assays.

An assay employing an antibody or antibodies, respectively, reactive to total proBNP, like monoclonal antibody MAB 17.3.1, 18.4.34, or 18.29.23, respectively, appears to detect all the proBNP molecules present in a serum sample, i.e., total proBNP. On the contrary, an assay based on an antibody reactive with native proBNP, e.g., MAB 1.21.3, only detects a fraction of this total proBNP.

It can be demonstrated by the present invention that the native proBNP subpopulation of total proBNP clinically shows a very good correlation to the biologically active BNP. Of course, in the measurement of BNP, all the precautions for obtaining correct BNP values with respect to sampling and handling have been observed. For measurement of native proBNP, routine sample processing without specific precautions proved satisfactory.

All the data established with the present invention clearly indicate that the epitope identified in the present invention and as specifically bound by MAB 1.21.3 is a major epitope for appropriate antibodies to native proBNP. Obviously, this native proBNP epitope as recognized by MAB 1.21.3 can undergo a natural modification or can become part of a protein complex which changes this epitope, with the effect that MAB 1.21.3 binds to such modified or complexed proBNP to a lower extent or not at all. The proBNP carrying such modified "non-native" proBNP epitope is only significantly measured in assays for total proBNP.

Because of their intrinsic high reproducibility, monoclonal antibodies are preferred tools to detect native proBNP. In a preferred embodiment, the present invention therefore relates to a monoclonal antibody specifically binding to native proBNP.

As the skilled artisan will appreciate, other monoclonal antibodies may be found which, compared to MAB 1.21.3, may show a slightly different pattern in reactivity to PepScan peptides numbers 35 to 38. A monoclonal antibody to native proBNP will not depart from the spirit of this invention as long as only a subpopulation of total proBNP is detected, which correlates with an r value of at least r=0.95 or above to the native proBNP subpopulation comprised in the total proBNP population and as bound by MAB 1.21.3. Such correlation is determined using the BIACORE system and the statistical assessment as described above. Even more preferred, such monoclonal antibody will detect essentially the same native proBNP subpopulation of total proBNP as bound by MAB 1.21.3, wherein the essentially the same subpopulation results in a correlation of r=0.98 or higher according to the above procedures. In a preferred embodiment, the present invention also relates to a method of producing a monoclonal antibody, the method comprising the steps of immunizing an appropriate non-human animal with proBNP, preferably a mouse, a rat, a rabbit, or a sheep, obtaining B-cells producing antibodies thereto, fusing these B-cells to appropriate fusion partners, and testing the antibodies produced by the hybridomas thus obtained for reactivity to native proBNP. Preferably only such monoclonal antibodies are selected and used in an immunoassay which in appropriate patient samples correlate to MAB 1.21.3 with an r value of at least 0.95. Such correlation is assessed as described above. Preferably the immunization is performed with synthetic proBNP or a proBNP produced in a prokaryotic host or with a synthetic peptide or fragments of proBNP, both at least comprising amino acids 41 to 44 of proBNP. Now that MAB 1.21.3 is available, it is of course also possible to produce, purify, and identify polyclonal antibodies which can be used in the specific detection of native proBNP. It has, e.g., been found that a polyclonal antibody to native proBNP can now be generated, purified, and characterized by its correlation to MAB 1.21.3.

As the skilled artisan will appreciate, there are various ways to produce a PAB which binds to native proBNP. Obviously it will, e.g., be possible to use one or more synthetic peptides as an immunosorbent in various successful routes of immunopurification.

Polyclonal antibodies to native proBNP will not depart from the spirit of this invention as long as only a subpopulation of total proBNP is detected, which correlates with an r value of at least r=0.95 or above to the native proBNP subpopulation comprised in the total proBNP population and as bound by MAB 1.21.3. Such correlation is determined using the BIACORE system and the statistical analysis as described above. Even more preferred, such polyclonal antibody preparation will detect essentially the same native proBNP subpopulation of total proBNP as bound by MAB 1.21.3, wherein such binding of the essentially the same subpopulation results in a correlation of r=0.98 or higher according to the above procedures.

One way to obtain such PAB to native proBNP is to immunize with recombinant or synthetically produced proBNP, to purify the native proBNP-specific antibodies therefrom by affinity purification, and to assess the polyclonal antibody thus obtained via patient samples as described above.

In a preferred embodiment, the present invention therefore relates to a method of producing polyclonal antibodies, the method comprising the steps of immunizing an appropriate non-human animal with proBNP, obtaining polyclonal antibodies thereto, and testing the antibodies thus obtained for reactivity to native proBNP. Preferably only such polyclonal antibodies are selected and used in an immunoassay for native proBNP which in appropriate patient samples correlate to MAB 1.21.3 with an r value of at least 0.95. Such correlation is assessed as described above.

For any polyclonal antibody specifically binding to native proBNP (using the same samples and procedures), the correlation to MAB 18.4.34, i.e., to total proBNP, will be significantly lower as compared to the correlation to MAB 1.21.3. Since polyclonal antibody preparations may always contain individual antibodies with different properties, preferably the correlation to MAB 18.4.34 for a polyclonal antibody specifically binding to the native proBNP subfraction of total proBNP will be r=0.94 or below. Even more preferred, it will be as low as 0.9 or below. Preferably polyclonal antibody preparations specifically binding to native proBNP will correlate to MAB 1.21.3 with r=0.98 or above and to MAB 18.4.34 with r=0.94 or below, or even more preferably, with r=0.9 or below to MAB 18.4.34. Preferably the immunization for obtaining polyclonal antibodies to native proBNP is performed with synthetic proBNP or a proBNP produced in a prokaryotic host or with a synthetic peptide or fragments of proBNP, both at least comprising amino acids 41 to 44 of proBNP. In the course of our experiments, a large variety of immunological reagents has been produced, analyzed, combined in various sandwich assays formats, and used in the detection of proBNP. These various combinations of immunological reagents revealed that the majority of assays appears to measure total proBNP.

The total proBNP assays investigated have been found to exhibit a reasonable correlation to BNP, which goes hand-in-hand with reasonable diagnostic accuracy for diagnosis of heart failure, cf. e.g., Mair, J. supra.

It could, however, now be established that an assay only detecting native proBNP, as compared to an assay detecting total proBNP, better differentiates between patients in NYHA class 0 or I and patients in NYHA classes II, III, or IV, respectively. This also leads to an improved clinical discrimination of heart failure patients.

In a preferred embodiment, the present invention therefore relates to a method for specific detection of native proBNP comprising the steps of contacting a sample suspected or known to contain proBNP with an antibody specifically binding to native proBNP under conditions allowing for the formation of an antibody to native proBNP-native proBNP complex and detecting the complex formed. Preferably said method for specific detection of native proBNP is used to differentiate NYHA stages 0 and I from NYHA stages II, II, or IV.

The "antibody to native proBNP-native proBNP complex" may also simply be termed "antibody-native proBNP complex".

The term "antibody" relates to mono- or polyclonal antibodies, chimeric, or humanized or other antibodies obtainable by genetic engineering, as well as all antibody fragments known to the expert such as F(ab')$_2$, Fab', or Fab fragments. Other binding agents with appropriate specificity for native proBNP can be used to substitute for antibodies or antibody fragments. Only the specific binding to native proBNP, in analogy to MAB 1.21.3, must be ensured.

As the skilled artisan appreciates, there are numerous ways to detect native proBNP employing an antibody specifically binding thereto, which all are described in detail in relevant textbooks (cf., e.g., Tijssen, P., Practice and Theory of Enzyme Immunoassays 11 (1990) Elsevier, Amsterdam, or Diamandis, et al., eds. (1996) Immunoassay, Academic Press, Boston).

In the context of the present invention, many reagents and reagent combinations for detection of total proBNP or native proBNP have been analyzed by the BIACORE system, some results of which are shown in the Specific Embodiments section.

In clinical routine diagnostics, frequently methods based on a heterogeneous immunoassay format are used. In a preferred embodiment according to the present invention, the method for detection of native proBNP is a competitive immunoassay.

Even more preferred are immunoassays according to the sandwich assay principle, in which an antibody-antigen-antibody complex, also called a sandwich, is formed.

In a preferred embodiment according to the present invention, the method for specific detection of native proBNP is a sandwich immunoassay, wherein a first antibody to native proBNP and a second antibody to total proBNP are used, and wherein the second antibody to proBNP and the first antibody to native proBNP both bind to native proBNP at different epitopes, thus forming a (first) anti-native proBNP antibody-native proBNP-(second) anti-proBNP antibody complex.

As the skilled artisan will appreciate, a sandwich assay for detection of native proBNP can also be set up using the antibody to total proBNP as a first (capture) antibody and the anti-native proBNP antibody as a second (tracer, detection, or labelled) antibody.

Preferably, such a sandwich method for determination of the native proBNP comprises the following steps:
(a) mixing a sample with a first native proBNP-specific antibody carrying a group suitable for binding to a solid phase or mixing the sample with the first native proBNP-specific antibody which is already bound to a solid phase,
(b) mixing this solution with a second antibody to total proBNP binding to an epitope outside the native proBNP epitope, which is present on both native proBNP and total proBNP, and carrying a label under conditions that a first antibody-native proBNP-second antibody complex is formed,
(c) binding the immune complex formed to a solid phase,
(d) separating the solid phase from the liquid phase, and
(e) detecting the label in one or both phases.

In a quantitative determination, the same measurement is carried out with a defined amount of native proBNP as a standard, and after the determination of the sample, a step (f) is performed, i.e., the measuring values of the standard or standard curve are compared to those obtained with the sample, and the corresponding concentration of native proBNP is extrapolated.

The first antibody specific for native proBNP can be bound directly to the solid phase or indirectly via a specific binding pair system. The direct binding of this antibody to the solid phase follows methods known to the expert, for example, in an adsorptive way. If the binding is indirect via a specific binding pair system, the first antibody is a conjugate consisting of an antibody against native proBNP and a first partner of the specific binding pair system. A "specific binding pair system" means two partners which can react specifically with each other. This binding can be based on an immunological binding or on an alternative specific binding. Preferred combinations are biotin and avidin, streptavidin or anti-biotin, respectively, hapten and anti-hapten, Fc-fragment of an antibody and antibodies against this Fc-fragment, or carbohydrate and lectin. Preferably, a combination of biotin and avidin or of biotin and streptavidin is used as a specific binding pair system.

The second partner of the specific binding pair system is coated to a solid phase. Streptavidin or avidin are used preferably. The binding of this partner of the specific binding pair system to an insoluble carrier material can be performed according to standard procedures known to the expert. Here a covalent as well as an adsorptive binding is suitable.

As a solid phase, test tubes or microtiter plates made of polystyrene or similar plastics are suitable which are coated with the second partner of the specific binding pair system. Further suitable and particularly preferred are particulate substances such as latex particles, magnetic particles, molecular sieve materials, and glass corpuscles. Paper or nitrocellulose can also be used as carriers. Use of magnetic beads coated with the second partner of the specific binding pair system as described above is particularly preferred. After completion of the immunological reaction and binding of the immunological complex formed to the solid phase, these microparticles can be separated from the liquid phase, for example, by filtration, centrifugation, or in the case of the magnetic particles, via a magnet. Detection of label bound to the solid phase, or of the label remaining in the liquid phase or of both, is then performed according to standard procedures.

The second antibody binding to total proBNP, binds to an epitope outside the native proBNP epitope which is present on both native proBNP and total proBNP. Simultaneous binding of both antibodies to these two epitopes on the native proBNP molecule must be possible because otherwise, no sandwich complex would form.

The investigators of the present invention have also identified epitopes on proBNP which are very appropriate for the sandwich assay described above.

A large number of monoclonal antibodies has been generated. It could be established that not all epitopes recognized on recombinant proBNP are equally appropriate to measure proBNP in a patient sample.

Three epitopes essentially consisting of amino acids 13-16, 27-31, and 64-67, respectively, as recognized by MAB's 17.3.1, 18.4.34, and 18.29.23, respectively, appear to be present on the vast majority of (N-terminal) proBNP molecules, i.e., are epitopes of total proBNP. These hybridomas have been deposited with the DSMZ on May 7, 2003. The antibodies produced by these hybridomas represent ideal tools for measurement of total proBNP. If used alone in a competitive assay format or in combination with each other or a PAB reacting with total proBNP in a sandwich assay format, total proBNP can be easily measured.

The preferred hybridoma cell lines according to the invention MAB<NT-proBNP>16.1.39(MAK<NT-proBNP>16.1.39=MAB 16.1.39), MAB<NT-proBNP>17.3.1, MAB<NT-pro BNP>1.21.3, MAB<NT-proBNP>18.4.34, and MAB<NT-proBNP>18.29.23, were deposited, under the Budapest Treaty on the international recognition of the deposit of microorganisms for the purposes of patent procedure, with Deutsche Sammlung von Mikroorganismen and Zellkulturen GmbH (DSMZ), Mascheroder Weg 1B, D-38124 Braunschweig, Germany, as follows:

| Cell line | Deposition no. | Date of deposit |
|---|---|---|
| MAK<NT-proBNP>17.3.1 | DSM ACC 2591 | May 7, 2003 |
| MAK<NT-proBNP>18.4.34 | DSM ACC 2592 | May 7, 2003 |
| MAK<NT-proBNP>18.29.23 | DSM ACC 2593 | May 7, 2003 |
| MAK<NT-proBNP>1.21.3 | DSM ACC 2650 | Apr. 27, 2004 |

The antibodies obtainable from said cell lines are preferred embodiments of the invention.

In the detection of native proBNP, preferably a monoclonal antibody to total proBNP as described above is used in a sandwich assay in combination with an antibody specifically binding to native proBNP. Such sandwich then results in an assay specifically detecting only the native proBNP subpopulation of total proBNP. Preferred antibodies to total proBNP in such sandwich for measurement of native proBNP are antibodies essentially binding to amino acids 13-16, 27-31, and 64-67, respectively. These epitopes, for example, are recognized by MAB's 17.3.1, 18.4.34, and 18.29.23, respectively. Most preferably an antibody binding to amino acids 27 to 31, like MAB 18.4.34, is used in such sandwich assay for native proBNP.

All biological liquids known to the expert can be used as a sample in a method for specific detection of native proBNP in vitro. The preferred samples for in vitro diagnosis are body fluids like whole blood, blood serum, blood plasma, urine, or saliva. The use of serum or plasma, respectively, is particularly preferred.

Besides the so-called wet tests as described above with test reagents in a liquid phase, all standard dry test formats suitable for the detection of antigens, haptens, peptides, proteins, antibodies, etc. can be used too. These dry tests or test strips, as for instance described in EP 186,799, combine all test components on one single carrier except the sample to be analyzed.

In a preferred embodiment, the present invention relates to a method for diagnosing heart failure comprising detecting native proBNP and correlating the level of native proBNP to the presence of heart failure. As the skilled artisan will appreciate, the level of native proBNP can also be used to assert the absence or the severity of heart failure.

It is also preferred to use a measurement of native proBNP in the follow-up of patients with heart failure and in the monitoring of treatment.

A further preferred embodiment relates to a kit for measurement of native proBNP comprising an antibody specifically binding to native proBNP and auxiliary reagents for detection of native proBNP.

The examples, references, sequence listing, and figures are provided to aid the understanding of the present invention, the true scope of which is set forth in the appended claims. It is understood that modifications can be made in the procedures set forth without departing from the spirit of the invention.

Specific Embodiments

EXAMPLE 1

Method of production of recombinant N-terminal proBNP (1-76)

Cloning of the Recombinant N-terminal proBNP

The nucleotide sequence of the N-terminal proBNP (amino acid sequence 1-76) was produced by means of genetic synthesis. To obtain an optimum expression of the gene in E. coli, the DNA sequence was suited to the codons most frequently used in E. coli. The sequences of the oligonucleotides used for the production of the gene are the following:

Pro5' (SEQ ID NO: 1):
5'CCGGATCCCACCCGCTG3'

Pro1hum (SEQ ID NO: 2):
5'CGGGATCCCACCCGCTGGGTTCCCCGGGTTCCGCTTCCGACCTGGAAA

CCTCCGGTCTGCAGGAACAGCGTAACACCTC3'

Pro2hum (SEQ ID NO: 3):
5'CGGTTCCAGGGAGGTCTGTTCAACCTGCAGTTCGGACAGTTTACCCTG

CAGGTGGTTACGCTGTTCCTGC3'

Pro3hum (SEQ ID NO: 4):
5'CAGACCTCCCTGGAACCGCTGCAGGAATCCCCGCGTCCGACCGGTGTT

TGGAAATCCCGTGAAGTTGCTAC3'

Pro4hum (SEQ ID NO: 5):
5'CCCAAGCTTAACGCGGAGCACGCAGGGTGTACAGAACCATTTTACGGT

GACCACGGATACCTTCGGTAGCAACTTCACGGGATTTCC3'

Pro3' (SEQ ID NO: 6):
5'CCCAAGCTTAACGCGGAGC3'

The production of the gene was carried out with these primers using polymerase chain reaction (PCR). The amplified gene was cloned in a suitable vector like, for example, the vector pUC19 and then sequenced. For the cloning of the gene in the expression vector pQE8, the gene was cut out of the vector pUC19 via the restriction cutting points Bam Hi and Hind III and then ligated in the vector pQE8 allowing an expression of proteins with N-terminal histidine tag and transformed in E. coli M15 [pREP4].

Expression of the N-terminal proBNP in E. coli

For the expression of the gene in E. coli, an over-night culture of a recombinant E. coli clone was transfected 1/60 in Luria broth (with 100 µg/ml ampicillin and 50 µg/ml kanamycin) and induced at an OD 550 of 1 with IPTG (isopropylthiogalactoside, 1 mM final concentration). After the induction, the cultures were further incubated for 4 hours at 37° C. The cultures were then centrifuged and the cell pellet gathered in 50 mM Na phosphate buffer, pH 8.0, 300 mM NaCl. After decomposition of the cell suspension via ultrasound, the suspension was centrifuged and the supernatant applied on a Ni-NTA (nitrile triacetate) column. After a washing step with 50 mM Na phosphate buffer, pH 8.0, 300 mM NaCl, 20 mM imidazole the histidine-tagged N-terminal proBNP was eluted with 50 mM Na phosphate buffer, pH 8.0, 300 mM NaCl, 300 mM imidazole. The eluted fractions were gathered and dialyzed against 50 mM Tris, pH 8.0. To separate impurities the dialysate was applied to a Q sepharose column. The mass of the purified N-terminal proBNP was determined via MALDI-TOF. This preparation (recombinant proBNP) was found to contain proBNP 1-76 and proBNP 1-66, the later most likely representing a degradation product.

EXAMPLE 2

Synthesis of NT-proBNP (1-76 amide)

NT-proBNP (1-76 amide) (SWISSPROT accession no. P16860, aa 27 to aa 134) was synthesized by an optimized solid phase peptide synthesis protocol (Merrifield (1962) Fed. Proc. Fed. Amer. Soc Exp. Biol. 21, 412) on an ABI 433 peptide synthesizer. In brief, the peptide was assembled on a Rink-linker modified polystyrene solid phase by repeatedly conjugating an eightfold excess of amino acids each protected by temporary piperidine labile Fmoc- and permanent acid labile tBu-, BOC-, OtBu-, Trt- or Pmc-groups depending on the side chain function. To get an oxidative stabile material the methionine at position 10 was exchanged by the equivalent amino acid norleucine. Further, to stabilize against proteolytic degradation the C-terminus was amidated by using the Rink linkage. After the assembly the fully protected peptide was removed from the solid phase and the permanent protecting groups were released by treatment with trifluoracetic acid in a mixture of suitable cation scavengers and finally isolated by preparative reverse phase HPLC purification. Three 125 μmol scale syntheses yielded 16.0, 17.1 and 18.0 mg RP-HPLC single peak pure material (lyophilisate), respectively. The identity was proven by MALDI- and ESI-mass spectroscopy [8439.4].

EXAMPLE 3

Production of and Screening for Monoclonal Antibodies Against Total or Native proBNP Obtaining Monoclonal Antibodies Against N-terminal proBNP Balb/c mice, 8-12 weeks old, are subjected to intraperitoneal immunization with 100 μg N-terminal proBNP antigen, with complete Freund's adjuvant. Recombinant as well as proBNP (1-76) produced synthetically by peptide synthesis, respectively, has been used as an antigen in mice. After 6 weeks three further immunizations are performed at 4-week intervals. One week after the last immunization blood is taken and the antibody titre is determined in the serum of the test animals. From the spleen of positively reacting mice, B-lymphocytes are obtained and subjected to fusion with a permanent myeloma cell line. The fusion is carried out according to the well-known method of Köhler and Millstein (Nature 256, 1975, p. 495-497). The primary cultures of the positive hybridomas are cloned in a usual way for example by using the commercially available cell sorter or by "limiting dilution".

For the production of ascites $5\times10^6$ hybridoma cells are intraperitoneally injected in Balb/c mice which had been treated 1-2 times with 0.5 ml Pristan before. After 2-3 weeks ascites liquid can be obtained from the abdominal region of the mice. From this, the antibodies can be isolated in the usual way.

Screening Test for Monoclonal Antibodies Against proBNP Peptides, Synthetic proBNP, and proBNP in Human Serum, Respectively To identify the presence of antibodies against proBNP in the culture supernatant of the hybridoma cells, supernatants are evaluated according to three screening assay formats.

Reactivity with Synthetic N-terminal proBNP

Microtiter plates (Nunc, Maxisorb) are bound with 2.5 μg/ml synthetic NT-proBNP as an antigen in a loading buffer (Coating buffer, Cat.No. 0726 559, Scil Diagnostics, GmbH) 100 μl/well, for 1 hour at room temperature under stirring. The post-loading is carried out in PBS buffer (phosphate buffered saline, Oxid, Code-BR 14a) and 1% Byco C, for 30 minutes. Subsequently, washing is performed with washing buffer (0.9m sodium chloride solution, 0.05% TWEEN 20). The antibody sample incubation is carried out with 100 μl/well for 1 hour at room temperature under stirring. A further washing step with washing solution takes place twice then. Afterwards, a further incubation is carried out with the detection antibody PAB<M-Fcy>goat-F(ab')$_2$-peroxidase conjugate (Chemicon, Cat. No. AQ127P), 100 mU/ml, 100 μl/well, for 1 hour at room temperature under stirring. After a further washing step with washing buffer the peroxidase activity is established in the usual way, for example, with ABTS, for 30 minutes at room temperature, and the extinction difference is read in mU at 405 nm by means of an ELISA reader.

Epitope Characterization Using Synthetic Peptides for Epitope Analysis

For epitope analysis, streptavidin-loaded microtiter plates are incubated with peptide-biotin conjugates derived from the sequence of proBNP (1-76). The complete proBNP sequence was scanned by applying 69 8-mer peptides shifted through the sequence in single amino acid steps, i.e., 1-8, 2-9, 3-10, 4-11 to 66-73, 67-74, 68-75, and 69-76, respectively. Additional biotinylated sequences have been tested comprising the amino acid positions 1-10, 8-18, 1-21, 16-30, 30-38, 3243, 39-50, 47-57, 50-63, 62-70, and 64-76, respectively. The individual antigenic peptides have been dissolved to 250 ng/ml in PBS buffer (phosphate buffered saline, Oxid, Code-BR 14a) with 0.5% Byco C. For peptide coating, 100 pl of each solution has been distributed in distinct wells of the microtiter plates which were then gently agitated for 1 hour under room temperature. Subsequently, washing was carried out with washing buffer (0.9m sodium chloride solution, 0.05% TWEEN 20). The antibody sample incubation and the detection reaction are performed as described above. Due to their reactivity with certain NT-proBNP peptides, the position of the epitope as recognized by a mono- or polyclonal antibody could be delineated.

Reactivity with proBNP in a Patient Sample

Wells of microtiter plates (Nunc, Maxisorb) are coated with 5 μg/ml PAB<human proBNP>S-IgG (IS, (1-21) or (30-38) S-IgG in loading buffer (Coating buffer, Cat.No. 0726 559, Scil Diagnostics, GmbH), 100 μl/well, for 1 hour at room temperature under stirring. The post-loading is carried out in PBS buffer (phosphate buffered saline, Oxid, Code-BR 14a) and 1% Byco C, for 30 minutes. Subsequently, washing is performed with washing buffer (0.9 sodium chloride solution, 0.05% TWEEN 20). The incubation with native antigen in patient plasma, diluted in PBS buffer, is carried out with 100 μl/well for 1 hour at room temperature under stirring. After a further washing step, the hybridoma supernatant incubation is performed with 100 μl/well for I hour at room temperature under stirring. Subsequently, washing is carried out twice with washing solution and a further incubation is performed with the detection antibody PAB<M-Fcy>Goat-F(ab')$_2$-peroxidase conjugate (Chemicon, Cat. No. AQ127P), 100 mU/ml, 100 μl/well, for 1 hour at room temperature under stirring. After a further washing step with washing buffer, the peroxidase activity is established in the usual way, for example, with ABTS, for 30 minutes at room temperature, and the extinction difference is read in mU at 405 nm by means of an ELISA reader. Only those hybridoma cultures have been further processed which reacted positively with synthetically produced N-terminal proBNP or with proBNP in human serum.

EXAMPLE 4

Production of Sheep Monoclonal Antibodies Against Pro BNP

Obtaining Monoclonal Sheep Antibodies Against N-terminal proBNP

Sheep were immunized with recombinant N-terminal proBNP in complete Freund's adjuvant. The dose was 0.1 mg per animal. The immunizations were repeated at 4-week intervals in a period of 10 months. Six weeks after the first immunization and afterwards once a month, the serum samples were obtained and tested for their sensitivity and titer.

The lymphocytes for fusions were obtained from lymph nodes of immunized sheep. Therefore 3 days before removal of the lymph node, a final boost injection with recombinant N-terminal proBNP was done directly into an inguinal sheep lymph node.

After surgical removal of the lymph node, the lymphocytes were prepared and isolated under sterile condition. About $2 \times 10^9$ cells from one lymph node were stored in liquid nitrogen at a density of $1 \times 10^8$ cells/vial.

For fusions, a vial of $1 \times 10^8$ frozen lymph node lymphocytes were thawed and mixed with hypoxanthine and thymidine sensitive myeloma/heteromyeloma cells (mouse NS1× sheep lymphocytes, clone 1 C 10, Bioventix, Inc.) in a ratio of 2:1 with fusing agent polyethylene glycol (PEG).

Several 96-well plates were seeded with $1-3 \times 10^4$ cells (or heteromyelomas) per well and cultivated in selection medium. After 8-10 days, examination and screening of the hybridoma cells for reactivity with N-terminal pro BNP were done by ELISA assay.

The primary cultures of the positive hybridomas were cloned in the usual way by using the commercially available cell sorter or by "limiting dilution".

Screening Test for Monoclonal Antibodies Against proBNP Peptides, Synthetic proBNP, and proBNP in Human Serum, Respectively To identify the presence of antibodies against proBNP in the culture supernatant of the hybridoma cells, supernatants were evaluated according to three screening assay formats.

Reactivity with Synthetic N-terminal proBNP

Microtiter plates (Nunc, Maxisorb) were coated with 2.5 µg/ml synthetic NT-proBNP as an antigen in a loading buffer (Coating buffer, Cat. No. 0726 559, Scil Diagnostics, GmbH) 100 µl/well, for 1 hour at room temperature under stirring. The post-loading was carried out in PBS buffer (phosphate buffered saline, Oxid, Code-BR 14a) and 1% Byco C, for 30 minutes. Subsequently, washing was performed with washing buffer (0.9 sodium chloride solution, 0.05% TWEEN 20). The antibody sample incubation was carried out with 100 µl/well for 1 hour at room temperature under stirring. A further washing step with washing solution then took place twice. Afterwards, a further incubation was carried out with the detection antibody peroxidase-conjugated AffiniPure Donkey Anti-Sheep IgG (Dianova Code Number 713-035-147) diluted 1:40,000 in PBS buffer, 100 µl/well, for 1 hour at room temperature under stirring. After a further washing step with washing buffe, the peroxidase activity was established in the usual way, for example, with ABTS for 30 minutes at room temperature, the extinction difference was read in mU at 405 nm by means of an ELISA reader.

Epitope Characterization Using Synthetic Peptides for Epitope Analysis

For epitope analysis, streptavidin-loaded microtiter plates were incubated with peptide-biotin conjugates derived from the sequence of proBNP(1-76).

The complete proBNP sequence was scanned by applying 69 8-mer peptides shifted through the sequence in single amino acid steps, i.e., 1-8, 2-9, 3-10, and 4-11 to 66-73, 67-74, 68-75, and 69-76, respectively. Additional biotinylated sequences were tested comprising the amino acid positions 1-10, 8-18, 1-21, 16-30, 30-38, 3243, 39-50, 47-57, 50-63, 62-70, and 64-76, respectively. The individual antigenic peptides were dissolved to 250 ng/ml in PBS buffer (phosphate buffered saline, Oxid, Code-BR 14a) with 0.5% Byco C. For peptide coating, 100 µl of each solution was distributed in distinct wells of the microtiter plates which were then gently agitated for 1 hour under room temperature. Subsequently, washing was carried out with washing buffer (0.9 M sodium chloride solution, 0.05% TWEEN 20). The antibody sample incubation and the detection reaction were performed as described above. Due to their reactivity with certain NT-proBNP peptides, the position of the epitope as recognized by a mono- or polyclonal antibody could be delineated.

An example of a PepScan is shown in FIG. 1. The monoclonal antibody secreted by hybridoma 1.21.3 strongly reacts with peptides numbers 39 through 42. This corresponds to a shared epitope consisting of the amino acids 41 through 46 (SEQ ID NO: 11) of proBNP.

Reactivity with proBNP in a Patient Sample

Wells of microtiter plates (Nunc, Maxisorb) were coated with 5 µg/ml MAB<human proBNP>M-18.4.34-IgG in loading buffer (Coating buffer, Cat.No. 0726 559, Scil Diagnostics, GmbH), 100 µl/well, for 1 hour at room temperature under stirring. The post-loading was carried out in PBS buffer (phosphate buffered saline, Oxid, Code-BR 14a) and 1% Byco C, for 30 minutes. Subsequently, washing was performed with washing buffer (0.9 sodium chloride solution, 0.05% TWEEN 20). The incubation with native antigen in patient plasma, diluted in PBS buffer, was carried out with 100 µl/well for 1 hour at room temperature under stirring. After a further washing step, the hybridoma supernatant incubation was performed with 100 µl/well for 1 hour at room temperature under stirring. Subsequently, washing was carried out twice with washing solution, and a further incubation with the detection antibody Peroxidase-conjugated AffiniPure Donkey Anti-Sheep IgG (Dianova Code Number 713-035-147), diluted 1:40 000 in PBS buffer, 100 mU/ml, 100 µl/well, for 1 hour at room temperature under stirring. After a further washing step with washing buffer, the peroxidase activity was established in the usual way, for example, with ABTS for 30 minutes at room temperature, the extinction difference read in mU at 405 nm by means of an ELISA reader.

Only those hybridoma cultures were further processed which reacted positively with synthetically produced N-terminal proBNP or with proBNP in human serum.

EXAMPLE 5

Production of Polyclonal Antibodies Against N-terminal proBNP

Immunization

Sheep were immunized with recombinant N-terminal proBNP (see Example 1) in complete Freund's adjuvant. The dose was 0.1 mg per animal. The immunizations were repeated at 4-week intervals in a period of 10 months. Six weeks after the first immunization and afterwards once a month, the serum samples were obtained and tested for their sensitivity and titer.

Purification of Polyclonal Antibodies from Sheep Serum

Starting from the raw serum of a sheep immunized with recombinant N-terminal proBNP, lipid components were removed by delipidation with aerosil (1.5%). Afterwards the immunoglobulins were separated by ammonium sulfate precipitation (2 M). The dissolved precipitate was dialysed against 15 mM KPO$_4$, 50 mM NaCl, pH 7.0, and chromatographed on DEAE sepharose. The IgG fraction (PAB<NT-proBNP>S-IgG(DE)) was obtained in the flow through.

Affinity chromatography for the Production of Polyclonal Antibodies Specific for Total proBNP For the affinity purification of polyclonal antibodies binding specifically to total proBNP (PAB<NT-proBNP>S-IgG (IS,1-21) or briefly, PAB<1-21>), the peptide HPLGSPG-SASDLETSGLQEQR-C ((1-21) 21-Cys, SEQ ID NO: 7) was used. The affinity matrix was produced by covalently binding I mg of the peptide (1-21)21-Cys to 2 ml of maleimide activated EAH-Sepharose 4B (Amersham Biosciences, Product No 17-0569-01).

With 10 ml of the affinity matrix, a column was packed and equilibrated with 50 mM $KPO_4$, 150 mM NaCl, pH 7.5 (PBS). Two g of PAB<NT-proBNP>S-IgG(DE) were applied to the column. The column was washed with PBS and 20 mM $KPO_4$, 500 mM NaCl, 0.1% TRITON X-100 (Rohm & Haas), 0.5% Na deoxicholic acid, pH 7.5. The IgG specifically bound to the affinity matrix was eluted with ImmunoPure Gentle Ag/Ab elution buffer (Pierce, Product No. 21013) and is referred to as PAB<1-21>. The affinity matrix was regenerated with 1 M propionic acid and conserved in $PBS/NaN_3$.

A similar procedure was applied to generate affinity purified polyclonal antibodies PAB<NT-proBNP>S-IgG (IS,30-38) or briefly, PAB<30-38>) specific for total proBNP (Karl, J. et al., WO 00/45176).

Affinity Chromatography for the Production of Polyclonal Antibodies Specific for Native proBNP The polyclonal antibody to native proBNP (PAB<NT-proBNP>S-IgG(IS,41-46), or briefly PAB<41-46 >) was obtained by sequential affinity chromatography. In the same way as described above, 3 individual peptides, CEUEU-SLE-PLQE ((37-43)37-Cys, SEQ ID NO: 8), CEUEU-SPRPT-GVW ((44-51)44-Cys, SEQ ID NO: 9) and C-EPLQE-SPRPTG ((39-50)39-Cys, SEQ ID NO: 10) (EUEU, SEQ ID NO: 12, merely functions as an extended linker for the peptide following behind) were used for the production of 3 individual affinity matrices. PAB<NT-proBNP>S-IgG(DE) was first applied to the affinity matrix comprising peptide (37-43) 37-Cys to remove all polyclonal antibody primarily binding to the NT-proBNP sequence 37-43. The flow through was then applied to the second affinity matrix comprising peptide (44-51)44-Cys to capture polyclonal antibodies primarily binding to the NT-proBNP sequence 44-51. The bound antibodies were eluted and collected as described above (PAB<44-5 1>). Finally, the flow through of the second affinity purification was passed over the third affinity matrix comprising peptide (39-50)39-Cys. The bound antibodies were eluted and collected as described above. As determined by the method known and referred to as PepScan analysis, the eluted antibodies from the third affinity matrix are specific for epitopes in the sequence 41-46 (PAB<41-46>) which represent the remaining epitopes of the overlapping sequence between 37-43 and 44-51.

EXAMPLE 6

BIACORE Analysis of Monoclonal and Polyclonal Antibodies to proBNP

The specificity of monoclonal and polyclonal antibodies to native NT-proBNP was determined by surface plasmon resonance using a BIACORE 3000 analyzer. All surface plasmon resonance measurements were performed at 25° C. using the BIACORE 3000 equipped with a research-grade CM5 sensor chip. The running buffer was HBS (10 mM HEPES, 150 mM NaCl, 3.4 mM EDTA and 0.005% P20 (Polysorbat) at pH 7.4).

Immobilization of the ligand PAB<NT-proBNP 1-21>S-IgG

The ligand which was used as capture antibody for total NT-proBNP was immobilized using amine-coupling chemistry. Before coupling, the sensor chip was preconditioned at a flow rate of 20 µl/min by 10 µl injections of 0.1% SDS, 50 mM NaOH, 10 mM HCI, and 100 mM phosphoric acid. The surfaces of all flow cells were activated for 5 min with a 1:1 mixture of 0.1 M NHS (N-hydroxysuccinimide) and 0.1 M EDC (3-(N,N-dimethyl-amino)propyl-N-ethylcarbodiimide) at a flow rate of 20 µl/min. The ligand at a concentration of 30 µg/ml in 10 mM sodium acetate, pH 5.0, was injected in all 4 flow cells for 5 min. The surfaces were blocked with a 5 min injection of 1 M ethanolamine, pH 8.0, followed by 30 s injections of HBSwash (100 mM HEPES, pH 7.4, 1.5 M NaCl, 3.4 mM EDTA, 0.05% P20 (Polysorbat), 2% DMSO), 100 mM HCI, and 2×100 mM phosphoric acid to remove noncovalently bound ligand. The density of the ligand was about 16,000 RU.

Concentration Measurements of NT-proBNP in Patient Samples

To perform the following method in BIACORE 3000, the program shown in FIG. 2 was used. Synthetic NT-proBNP(1-76)amid in concentrations of 0, 2.5, 5, 10, 20, and 40 nM in 20% horse serum (horse serum diluted 1:5 with HBS+1 mg/ml carboxymethyldextran) was used as calibrator. The addition of carboxymethyldextran was used to suppress non-specific binding of serum components to the surface of the sensor chip).

Patient samples with >10 ng/ml native NT-proBNP were diluted 1:5 with HBS also containing 1 mg/ml carboxymethyldextran.

Calibrator and patient samples were injected at a flow rate of 10 µl/min for 10 min over all four flow cells followed by a 30 s injection of HBS at a flow rate of 100 µl/min to remove non-specifically bound serum components. The antibody whose specificity had to be determined was injected in a concentration of 500 nM in HBS for 3 min at a flow rate of 10 µl/min, antibody 1 in flow cell 1, antibody 2 in flow cell 2, and so on. The binding data of the antibodies in RU were determined as difference between the response 10 s before the injection of an antibody and the response 10 s before the injection of the next antibody or HBS, respectively.

For the calculation of the NT-proBNP concentrations in the patient samples, BIA evaluation software v. 4.1 was used. For each antibody, a calibration curve of synthetic NT-proBNP (1-76)amid was generated using a spline fit, and the corresponding concentrations of the 1:5 diluted patient samples were calculated. The concentrations were multiplied by 5 to get the concentrations of NT-proBNP in undiluted sera.

Determination of the Specificity of an Antibody

In order to determine if an antibody binds to native or total NT-proBNP in human serum, the concentrations of NT-proBNP determined with the antibody in question (y-axis) were plotted against the concentrations of the corresponding sample determined with the reference antibody MAB 1.21.3 (x-axis). A linear regression curve of the type y=ax+b was fitted using Microsoft Excel and the coefficient of correlation r and the slope were calculated.

TABLE 1

Characteristics of various anti-proBNP antibodies

| Antibody | Epitope recognized | Synthetic proBNP | Patient sample proBNP |
|---|---|---|---|
| MAB 17.3.1 | amino acids 13-16 | +++ | +++ |
| MAB 18.4.34 | amino acids 27-31 | +++ | +++ |
| MAB 18.29.23 | amino acids 62-76 | +++ | +++ |

TABLE 1-continued

Characteristics of various anti-proBNP antibodies

| Antibody | Epitope recognized | Synthetic proBNP | Patient sample proBNP |
| --- | --- | --- | --- |
| MAB 1.21.3 | amino acids 42-46 | +++ | + |
| PAB<1-21> | amino acids 1-21 | +++ | +++ |
| PAB<44-51> | amino acids 44-51 | +++ | ++ |
| PAB<41-46> | amino acids 41-46 | +++ | + |

+++ indicates that both synthetic proBNP and proBNP in a patient sample are recognized very well and to a similar extend
+ indicates a reaction in the range of 15% with proBNP in a patient sample as compared to the value obtained with synthetic proBNP From Table 1, it is readily evident that the vast majority of proBNP epitopes appears to be present on synthetic proBNP and proBNP as comprised in a patient sample in the same manner. This is exemplified by MAB 17.3.1, MAB 18.4.34, MAB 28.29.13, and PAB <1-21>, respectively. One epitope, however, appears not to be present on synthetic proBNP and proBNP as comprised in a patient sample in the same manner. This epitope essentially consists of amino acids 41-44 and is recognized by MAB 1.21.3 as well as by PAB <41-46>. It appears that, using these immunological reagents, only a subpopulation of the total proBNP as present in a patient sample is recognized. This leads to strikingly different results when measuring proBNP in a patient sample with an assay for total proBNP or an assay for native proBNP, respectively. Only this subpopulation of total proBNP appears to carry an epitope characteristic for native proBNP.

As is obvious from FIGS. 3 to 8, all antibodies to native proBNP, i.e., MAB 16.1.39 and PAB<41-46>, show a very good correlation to MAB 1.21.3, whereas the antibodies to total proBNP, i.e., MAB 18.4.34, MAB 18.29.23, and PAB 30-38, show a much lower correlation to MAB 1.21.3. PAB <44-51>interestingly appears to be of somewhat mixed reactivity and would not qualify as an antibody specifically binding to native proBNP because it correlates to less than r=0.95 to MAB 1.21.3.

EXAMPLE 7

Clinical Comparison of Assays for Native and Total proBNP

In a clinical study, 246 patient samples classified according to their NYHA status have been analyzed by sandwich immunoassays for native proBNP and total proBNP, respectively. The results of this study are given in Table 2.

TABLE 2

Comparative analysis of native proBNP and total proBNP in patient samples

| NYHA | n 246 | Native proBNP arbitrary units | NYHA X/ NYHA 0 | Total proBNP pg/ml | NYHA X/ NYHA 0 |
| --- | --- | --- | --- | --- | --- |
| 0 | 119 | 337 | 1.0 | 638 | 1.0 |
| 1 | 32 | 355 | 1.1 | 717 | 1.1 |
| 2 | 62 | 655 | 1.9 | 1072 | 1.7 |
| 3 | 30 | 2947 | 8.7 | 3609 | 5.6 |
| 4 | 3 | 12755 | 38 | 15902 | 25 |

Clinically very important is the differentiation of patients with no or very mild disease (HYHA classes 0 and 1) as compared to patients with disease progression (NYHA X=classes 2 or more). As can be seen from Table 2, there is a significant increase from class 0/1 to class 2 and higher classes. This increase for all the classes 2, 3, and 4 is more pronounced for native proBNP as compared to total proBNP. This translates to a better sensitivity/specificity profile and clinical utility for native proBNP as compared to total proBNP.

What is claimed is:

1. A monoclonal antibody that binds specifically to an epitope present on a subfraction of pro-brain natriuretic peptide (proBNP) and which measures a subfraction of proBNP present in a sample with a linear correlation coefficient of at least 0.95 to measurement of the subfraction of proBNP present in the sample by a reference monoclonal antibody produced by hybridoma DSM ACC 2650, wherein the epitope consists of amino acids 41-46 (SEQ ID NO: 11) of proBNP.

2. A method for measuring a subfraction of pro-brain natriuretic peptide (proBNP) comprising the steps of contacting a sample suspected or known to contain said subfraction of proBNP with a monoclonal antibody that binds specifically to an epitope present on a subfraction of proBNP and which measures a subfraction of proBNP present in a sample with a linear correlation coefficient of at least 0.95 to measurement of the subfraction of proBNP present in the sample by a reference monoclonal antibody produced by hybridoma DSM ACC 2650, wherein the epitope consists of amino acids 41-46 (SEQ ID NO: 11) of proBNP, the contacting being under conditions allowing for formation of a complex comprising the monoclonal antibody and the subfraction, and detecting the complex formed as a measure of the subfraction of proBNP.

3. A method for diagnosing heart failure in a patient comprising measuring a subfraction of pro-brain natriuretic peptide (proBNP) in a sample of plasma or serum from the patient according to the method of claim 2 and correlating an increased level of the subfraction measured in the sample to an increased severity of heart failure in the patient.

4. A kit for measurement of a subfraction of pro-brain natriuretic peptide (proBNP) comprising a monoclonal antibody that binds specifically to an epitope present on a subfraction of proBNP and which measures a subfraction of proBNP present in a sample with a linear correlation coefficient of at least 0.95 to measurement of the subfraction of proBNP present in the sample by a reference monoclonal antibody produced by hybridoma DSM ACC 2650, wherein the epitope consists of amino acids 41-46 (SEQ ID NO: 11) of proBNP.

* * * * *

SEQUENCE LISTING

<160> NUMBER OF SEQ ID NOS: 12

<210> SEQ ID NO 1
<211> LENGTH: 17
<212> TYPE: DNA
<213> ORGANISM: Escherichia coli

<400> SEQUENCE: 1
ccggatccca cccgctg                                                17

<210> SEQ ID NO 2
<211> LENGTH: 79
<212> TYPE: DNA
<213> ORGANISM: Escherichia coli

<400> SEQUENCE: 2
cgggatccca cccgctgggt tccccgggtt ccgcttccga cctggaaacc tccggtctgc    60
aggaacagcg taaccacct                                              79

<210> SEQ ID NO 3
<211> LENGTH: 70
<212> TYPE: DNA
<213> ORGANISM: Escherichia coli -continued

```
<400> SEQUENCE: 3
cggttccagg gaggtctgtt caacctgcag ttcggacagt ttaccctgca ggtggttacg    60
ctgttcctgc                                                           70

<210> SEQ ID NO 4
<211> LENGTH: 71
<212> TYPE: DNA
<213> ORGANISM: Escherichia coli

<400> SEQUENCE: 4
cagacctccc tggaaccgct gcaggaatcc ccgcgtccga ccggtgtttg gaaatcccgt    60
gaagttgcta c                                                         71

<210> SEQ ID NO 5
<211> LENGTH: 87
<212> TYPE: DNA
<213> ORGANISM: Escherichia coli

<400> SEQUENCE: 5
cccaagctta acgcggagca cgcagggtgt acagaaccat tttacggtga ccacggatac    60
cttcggtagc aacttcacgg gatttcc                                        87

<210> SEQ ID NO 6
<211> LENGTH: 19
<212> TYPE: DNA
<213> ORGANISM: Escherichia coli

<400> SEQUENCE: 6
cccaagctta acgcggagc                                                 19

<210> SEQ ID NO 7
<211> LENGTH: 22
<212> TYPE: PRT
<213> ORGANISM: Homo sapiens

<400> SEQUENCE: 7

His Pro Leu Gly Ser Pro Gly Ser Ala Ser Asp Leu Glu Thr Ser Gly
 1               5                  10                  15

Leu Gln Glu Gln Arg Cys
            20

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Beta-Ala
<220> FEATURE:
<221> NAME/KEY: MOD_RES
<222> LOCATION: (5)
<223> OTHER INFORMATION: Beta-Ala

<400> SEQUENCE: 8

Cys Glu Xaa Glu Xaa Ser Leu Glu Pro Leu Gln Glu
 1               5                  10
```

-continued

```
<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Beta-Ala
<220> FEATURE:
<221> NAME/KEY: MOD_RES
<222> LOCATION: (5)
<223> OTHER INFORMATION: Beta-Ala

<400> SEQUENCE: 9

Cys Glu Xaa Glu Xaa Ser Pro Arg Pro Thr Gly Val Trp
  1               5                   10

<210> SEQ ID NO 10
<211> LENGTH: 12
<212> TYPE: PRT
<213> ORGANISM: Homo sapiens

<400> SEQUENCE: 10

Cys Glu Pro Leu Gln Glu Ser Pro Arg Pro Thr Gly
  1               5                   10

<210> SEQ ID NO 11
<211> LENGTH: 6
<212> TYPE: PRT
<213> ORGANISM: Escherichia coli

<400> SEQUENCE: 11

Leu Gln Glu Ser Pro Arg
  1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-Ala
<220> FEATURE:
<221> NAME/KEY: MOD_RES
<222> LOCATION: (4)
<223> OTHER INFORMATION: Beta-Ala

<400> SEQUENCE: 12

Glu Xaa Glu Xaa
  1
```